United States Patent [19]

Ohnishi et al.

[11] Patent Number: 5,350,775
[45] Date of Patent: Sep. 27, 1994

[54] BENZOPYRAN DERIVATIVE, METHOD FOR PRODUCING THE SAME AND USE THEREOF

[75] Inventors: Yutaka Ohnishi; Naoaki Misu; Yoshimasa Ishimura, all of Kanagawa; Nobutake Mihara, Tokyo, all of Japan

[73] Assignee: Showa Denko K.K., Tokyo, Japan

[21] Appl. No.: 89,561

[22] Filed: Jul. 12, 1993

[30] Foreign Application Priority Data

Jul. 20, 1992 [JP] Japan ................... 4-192480

[51] Int. Cl.$^5$ ................ A61K 31/665; C07F 9/09
[52] U.S. Cl. ................................... 549/220
[58] Field of Search ............ 549/220; 514/844, 100

[56] References Cited

FOREIGN PATENT DOCUMENTS 0236120 3/1987 European Pat. Off. .

OTHER PUBLICATIONS

Chem. Pharm. Bull., 19, (4), pp. 687–695, (1971).

Primary Examiner—Nicky Chan
Attorney, Agent, or Firm—Sughrue, Mion, Zinn, Macpeak & Seas

[57] ABSTRACT

A benzopyran derivative represented by formula (I):

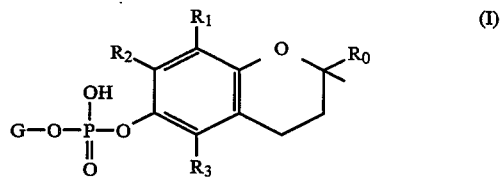

wherein $R_0$ represents an alkyl or alkenyl group having 10 to 20 carbon atoms, $R_1$ to $R_3$ each represent a methyl group or a hydrogen atom, and G represents a —$CH_2CH(OH)CH_2OH$ or —$CH(CH_2OH)_2$ group; or a salt thereof, which has a high water-solubility and thus is usable in cosmetics.

7 Claims, No Drawings

BENZOPYRAN DERIVATIVE, METHOD FOR PRODUCING THE SAME AND USE THEREOF

FIELD OF THE INVENTION

This invention relates to a novel benzopyran derivative and its salt. More particularly, it relates to a 3,4-dihydrobenzopyran derivative capable of giving a salt which has a relatively high water-solubility and thus is usable in the fields of, for example, cosmetics.

BACKGROUND OF THE INVENTION

Since being found as a murine antisterility vitamin, tocopherol has been importantly used as a substance having pharmacological activities over a wide range not only in the field of medicines but also in the fields of foods, cosmetics, fisheries and livestock industry.

However tocopherol is a viscous, fat-soluble compound and unstable to oxygen, heat, light and alkalis, which restricts application thereof. Thus attempts have been made to solve these problems by using tocopherol in the form of derivatives which are stable to oxygen, for example, esters such as acetate and nicotinate. However, these esters are insoluble in water, similar to tocopherol.

It has been reported that 70 mg of α-tocopheryl phosphoacetate sodium salt can be dissolved in 1 ml of water (JP-B-45-21711, the term "JP-B" as used herein means an examined Japanese patent application. Characteristics of tocopherol phosphate ethylene glycol derivatives in relation to water are also described in Yakugaku Zasshi, 75 (11), 1322 (1955), and Chem. Pharm. Bull., 19 (4), 687 (1971). However, the former suffers from a disadvantage that the solution becomes turbid under neutral conditions, and the latter exhibits only a low water solubility of 0.02% in the form of diethylene glycol ester. In the latter case, a pentaethylene glycol ester shows a high water-solubility of 9.6%, but it is necessary to use a phosphorylating agent together, the synthesis of which is difficult and requires complicated procedures involving several steps.

SUMMARY OF THE INVENTION

An object of the present invention is to provide a benzopyran derivative, for example, a tocopherol derivative, which is soluble in water under neutral conditions, has a high stability and can be easily produced, a method for producing the same and a use thereof.

The present inventors have conducted extensive studies and, as a result, succeeded in the production of a benzopyran derivative which is an ester of 1 mol of a 3,4-dihydrobenzopyran-6-ol and 1 mol of glycerol bonded to 1 mol of phosphoric acid.

That is, the present invention provides a benzopyran derivative represented by formula (I):

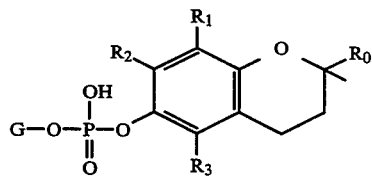

wherein $R_0$ represents an alkyl or alkenyl group having 10 to 20 carbon atoms; $R_1$ to $R_3$ each represent a methyl group or a hydrogen atom; and G represents a —$CH_2CH(OH)CH_2OH$ or —$CH(CH_2OH)_2$ group.

DETAILED DESCRIPTION OF THE INVENTION

In formula (I), $R_0$ preferably represents —$C_{16}H_{33}$. Namely, a preferred example of the benzopyran derivative of the present invention is a tocopherol derivative.

The benzopyran derivative represented by formula (I) and its salt can be produced by reacting a compound represented by formula (II):

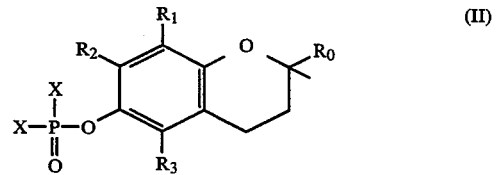

wherein $R_0$ represents an alkyl or alkenyl group having 10 to 20 carbon atoms; $R_1$ to $R_3$ each represent a methyl group or a hydrogen atom; and X represents a halogen atom; with a compound represented by formula (III-1) or (III-2):

wherein $R_4$ and $R_5$ each represent a protective group of a hydroxyl group; eliminating the protective groups to provide hydroxyl groups, and optinally converting the resulting product into a salt.

Preferable examples of the halogen atom represented by X in formula (II) are a chlorine atom and a bromine atom.

The protective groups of a hydroxyl group represented by $R_4$ and $R_5$ in formulae (III-1) and (III-2) are not particularly restricted, so long as they can serve as a protecting group and provide a hydroxyl group. Preferred examples of the protective group include alkoxyalkyl groups having a $C_{1-3}$ alkoxy moiety and a $C_{1-3}$ alkyl moiety, such as methoxymethyl and ethoxyethyl groups. Alternately, $R_4$ and $R_5$ may bond together to form ketals such as isopropylidene or cyclohexylidene, or acetals such as benzylidene.

Hereinafter, the present invention is explained merely with reference to the preferred benzopyran derivative, i.e., a tocopherol derivative, and its salt, but it is not limited thereto.

The compound of formula (II) wherein $R_0$ is —$C_{16}H_{33}$ (hereafter referred to as "formula (II')") to be used as a starting material in the reaction can be prepared by reacting a tocopherol with a phosphorylating agent such as phosphoric acid monoester dihalogenoide, phosphorus oxytrichloride or phosphorus oxytribromide in a solvent. The phosphorylating agent is used in an amount of from 1 to 5 mols, preferably from 1 to 1.3 mols, per mol of tocopherol. As the reaction solvent, an inert solvent such as benzene, toluene, tetrahydrofuran, diethyl ether, isopropyl ether and methyl tert-butyl ether may be used. The reaction is performed at a temperature ranging from −20° to 50° C., preferably 0° to 30° C., for 1 to 24 hours. In order to trap hydrogen halide formed during the reaction, a base such as pyridine, triethylamine, sodium carbonate or potassium carbonate may be added to the reaction system as a deacidifying agent generally in an amount of from 1 to 5 mols, preferably from 1 to 2 mols, per mol of tocopherol used.

Tocopherols are represented by the following formula and there are known tocopherol homologues depending on the substituents $R_1$, $R_2$ and $R_3$.

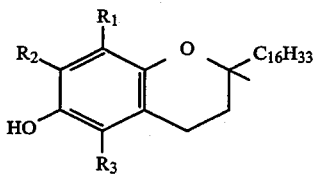

These homologues include α-tocopherol ($R_1$, $R_2$, $R_3$=CH$_3$), β-tocopherol ($R_1$, $R_3$=CH$_3$, $R_2$=H), γ-tocopherol ($R_2$, $R_3$=CH$_3$, $R_1$=H), δ-tocopherol ($R_3$=CH$_3$, $R_1$, $R_2$=H), ζ$_2$-tocopherol ($R_1$, $R_2$=CH$_3$, $R_3$=H) and η-tocopherol ($R_1$, $R_3$=H, $R_2$=CH$_3$) There are also known ζ$_1$-tocopherol and ε-tocopherol wherein the long chain alkyl group binding to the carbon atom adjacent to the oxygen atom in the benzopyran structure of α-tocopherol or β-tocopherol is substituted by the following group:

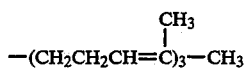

Each of these tocopherols is usable as a starting compound for preparing a compound of formula (II'). Among these compounds, α-tocopherol is particularly preferred.

The compound represented by formulae (III-1) and (III-2) can be prepared by, for example, the following method.

When glycerol is to be used as a starting material, glycerol is first reacted with a ketone or an aldehyde (e.g., acetone, benzaldehyde, cyclohexanone, methyl ethyl ketone or diethyl ketones) or a ketal or an acetal (e.g., 2,2-dimethoxypropane or , α,α-dimethoxytoluene).

This reaction is carried out in a solvent such as benzene or toluene in the presence of an acidic catalyst. Examples of the catalyst include hydrochloric acid, sulfuric acid, acetyl chloride and p-toluenesulfonic acid. The reaction temperature ranges from room temperature to the reflux point of the solvent, generally from 20° to 150° C., preferably from 60° to 120° C., while the reaction time ranges from 1 to 24 hours, preferably from 1 to 10 hours and more preferably from 1 to 2 hours.

The reaction between a compound represented by formula (II') and a compound represented by formula (III-1) or (III-2) may be carried out under almost the same conditions as those employed in preparation of a compound of formula (II') as described above. Namely, an inert solvent such as benzene, toluene, tetrahydrofuran, diethyl ether, isopropyl ether and methyl tert-butyl ether may be used as a solvent. The reaction time is from 1 to 10 hours, preferably from 1 to 3 hours, and the reaction temperature ranges from −30 ° C. to the reflux point of the solvent, preferably from 0° to 50° C. and more preferably from 0° to 30° C. Similar to the above-mentioned case, a base such as pyridine, triethylamine, sodium carbonate or potassium carbonate may be added to the reaction system as a trapping agent for hydrogen halide formed during this reaction. The amount of the base is preferably from 1 to 2 mols per mol of the compound of formula (II').

After completion of the reaction, the reaction product is subjected to a protective group-eliminating treatment, which varies depending on the protective groups to be eliminated. In general, the protective group-eliminating treatment can be effected by treating the reaction product dissolved in a solvent in the presence of an acidic catalyst or a hydrogenating catalyst while stirring. For example, when $R_4$ ad $R_5$ are alkoxyalkyl-groups (e.g., methoxymethyl and ethoxymethyl, respectively, or bond together to form a ketal or an acetal, elimination of the protective group can be effected by treating the reaction product in water or a mixed solvent comprising water with methanol, ethanol, tetrahydrofuran or dioxane in the presence of an acidic catalyst such as hydrochloric acid, sulfuric acid, phosphoric acid, acetic acid, p-toluenesulfonic acid, methanesulfonic acid or camphorsulfonic acid within a temperature range of from about 10° to 80° C. for 1 to 2 hours.

When $R_4$ and $R_5$ bond to form a benzylidene, elimination of the protective group can be completed by catalytically hydrogenating the reaction product in a polar solvent such as water, methanol, ethanol, formic acid, acetic acid, dimethylformamide or a mixture thereof in the presence of a catalyst such as nickel, palladium, platinum, rhodium or cobalt under a pressure of from 1 to 100 atm at a temperature of from −20° to 80° C., preferably from 0° to 50° C., for 1 to 5 hours.

By the above-mentioned treatment, the tocopherol derivatives of the present invention can be obtained as admixture of α-compound [G: —CH$_2$CH(OH)CH$_2$OH] and β-compound [G: —CH(CH$_2$OH)$_2$]

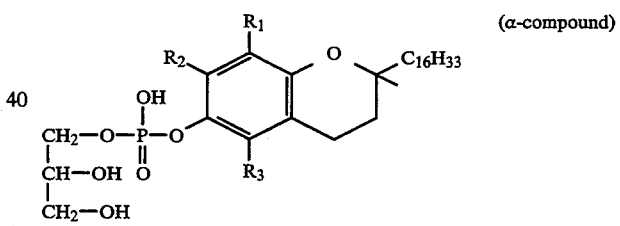
(α-compound)

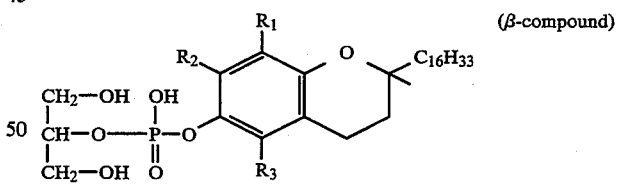
(β-compound)

If desired, the α-compound can be solely obtained by treating the reaction product with an alkali aqueous solution prior to the protective group-eliminating treatment. For the purpose, sodium hydroxide and potassium hydroxide are preferably used. The alkali aqueous solution has an alkali concentration of 0.5N to 5N, preferably 1 to 3N, and is generally used in an amount of 2 to 5 mols, preferably 2.5 to 3.5 mols, per mol of phosphorylating agent used in preparation of the compound of formula (II').

The thus obtained tocopherol derivative represented by formula (I) has a low toxicity and can be used as such in, for example, cosmetics.

If desired, it can be converted into pharmacologically acceptable salts by a known method, involving a step of mixing the tocopherol derivative with a base in an organic solvent or a mixed solvent of water and an organic solvent. These salts are not particularly restricted, so long as they are nontoxic, and examples include alkali metal salts such as sodium and potassium salts, alkaline earth metal salts such as calcium and magnesium salts, and ammonium salt. In the casee of forming alkali metal salts, for instance, one part by weight of the tocopherol derivative is dissolved in 0.25 to 5 parts by weight of an orgaic solvent such as alcohols (e.g., methanol and ethanol), to which a solution containing 0.5 to 1.5 mol, preferably 0.9 to 1.1 mol, per mol of tocopherol derivative, of a hydroxide (e.g., sodium hydroxide and pottasium hychoxide) in water or in an organic solvent such as alcohols is dropwise added. The hydroxide concentration of the solution is preferably as low as 1 to 5N so as to prevent decomposition of the tocopherol derivative. The dropwise addition is generally carried out at a temperature of from 0° to 50° C. and preferably from 10° to 30° C.

The tocopherol derivative of the present invention and a salt thereof, wherein tocopherol binds to glycerol via phosphate, have the inherent effects of tocopherol such as an antioxidation effect and a blood circulation promoting effect, and the moisture-retention effect of glycerol and, in addition, an improved water-solubility.

The tocopherol derivative of the present invention and a salt thereof cause neither skin irritation nor allergic reaction and have a high safety to the skin, which makes it highly useful in, for example, cosmetics.

The benzopyran derivatives of formula (I), other than the tocopherol derivatives, and their salts can be obtained and applied in the same manner as described above without difficulties.

The present invention is further explained in greater detail with reference to the following Examples, Formulation Examples and Test Examples. However, it is to be understood that the present invention is not restricted thereto.

EXAMPLE 1

18.40 g of phosphorus oxytrichloride was dissolved in 80 ml of toluene. To the obtained solution was added dropwise a mixture of 25.0 g (0.058 mol) of DL-$\alpha$-tocopherol and 9.50 g of pyridine dissolved in 80 ml of toluene under stirring at room temperature. After completion of the addition, the mixture was stirred for additional 3 hours. The pyridine hydrochloride thus precipitated was separated by filtration and the filtrate was concentrated under reduced pressure.

To the oily residue was added 80 ml of toluene and stirred in an oil bath at 70° C. Then a mixture of 12.25 g (0.092 mol) of 2,2-dimethyl-1,3-dioxolane—4-methanol protected at the 1- and 2-positions of glycerol and 9.50 g of pyridine dissolved in 80 ml of toluene was added dropwise thereto. After completion of the addition, the mixture was stirred for additional 3 hours and then cooled to room temperature. After cooling, the pyridine hydrochloride thus precipitated was separated by filtration and the filtrate was concentrated under reduced pressure.

The oily residue thus obtained was dissolved in 250 ml of ethyl acetate and washed four times with 250 ml of an aqueous solution of common salt. Then, the organic layer was dried over sodium sulfate.

The dried organic layer was concentrated under reduced pressure and dissolved in 50 ml of methanol. Then, 50 ml of 1N hydrochloric acid was added thereto and the mixture was heated to 50° C. for 30 minutes under stirring. The reaction mixture was concentrated under reduced pressure and the oily residue thus obtained was treated by silica gel chromatography. The solvent in the fraction was distilled off and thus 8.0 g of phosphoric acid diester was obtained. $^1$H-NMR (CDCl$_3$, $\delta$ ppm):

0.86 (d, 12H methyl proton),
1.75 (t, 2H methylene proton),
2.04, 2.10, 2.13 (s, 9H methyl proton),
2.55 (t, 2H methylene proton),
3.50–4.30 (m, 5H glycerol site, methylene proton and methyl proton).

$^{31}$P-NMR (internal phosphoric acid standard, CDCl$_3$, $\delta$ ppm):

4.23 ($\alpha$-compound)

EXAMPLE 2

The phosphoric acid diester obtained in Example 1 was dissolved in 20 ml of methyl alcohol. Then, 13 ml of a methyl alcohol solution of 1N sodium hydroxide was slowly added dropwise thereto at room temperature.

After completion of the addison, the thus obtained solution was added dropwise to 300 ml of acetone, and white precipitate formed was washed with 50 ml of acetone and dried. Thus 6.2 g of white powdery crystals were obtained. $^1$H-NRM (CD$_3$OD, $\delta$ ppm):

0.85 (d, 12H methyl proton),
1.73 (t, 2H methylene proton),
2.05, 2.10, 2.14 (s, 9H methyl proton),
2.55 (t, 2H methylene proton),
3.50–4.30 (m, 5H glycerol site, methylene proton and methyl proton).

$^{31}$P-NMR (internal phosphoric acid standard, CD$_3$OD, $\delta$ ppm):

3.21 ($\alpha$-compound),
3.35 ($\beta$-compound).

FT-IR (KBr, cm$^{-1}$)

| FT-IR (KBr, cm$^{-1}$) | |
|---|---|
| 3300–2800 | br. s P(O)OH |
| 2932 | C—H stretching vibration |
| 1230 | P=O stretching vibration (phosphate) |
| 945 | P—O—C stretching vibration (aromatic) |

EXAMPLE 3

The phosphoric acid diester obtained in Example 1 was dissolved in 20 ml of methyl alcohol. Then, 13 ml of a methyl alcohol of 1N potassium hydroxide was slowly added dropwise thereto at room temperature. After completion of the addison, the thus obtained solution was added dropwise to 300 ml of acetone. White precipitate thus formed was washed with 50 ml of acetone and dried, whereby 5.3 g of a white solid was obtained.

$^1$H-NMR (CD$_3$OD, $\delta$ppm):

0.86 (d, 12H methyl proton),
1.73 (t, 2H methylene proton),
2.05, 2.10, 2.14 (s, 9H methyl proton),
2.56 (t, 2H methylene proton),
3.50–4.30 (m, 5H glycerol site, methylene proton and methyl proton).

−P-NMR (internal phosphoric acid standard, CD$_3$OD, $\delta$ ppm):

3.20 ($\alpha$-compound)
3.34 ($\beta$-compound).

| FT-IR (KBr, cm$^{-1}$) | |
|---|---|
| 3300–2800 | Br. s P(O)OH |
| 2930 | C—H stretching vibration |
| 1230 | P=O stretching vibration (phosphate) |
| 945 | P—O—C stretching vibration (aromatic). |

EXAMPLE 4

4.89 g (0.0319 mol) of phosphorus oxychloride and 4.59 g of pyridine were subsequently added in a reactor, to which a solution containing 12.5 g (0.0290 mol) of DL-α-tocopherol in 50 mol of methyl tert-butyl ether was dropwise added while cooling with ice, followed by stirring for 3 hours. Then, a mixture of 4.63 g (0.0350 mol) of 2,2-dimethyl-1,3-dioxolane-4-methanol and 4.59 g of pyridine was added thereto with ice-cooling, followed by stirring for additional 3 hours. Thereafter, 50 ml of methyl tert-butyl ether was added to the reaction solution, to which 100 ml of an aqueous solution of 1N sodium hydroxide was then added dropwise and stirred for 1 hour.

After stirring, an aqueous phase separated was discarded and the remaining organic phase was washed with 100 ml of 1N hydrochloric acid three times. Then, the solvent of the resultant was removed under reduced pressure and the residue was mixed with 100 ml of ethanol and 3 mols of 2N hydrochloric acid and allowed to react at 50° C. for 2 hours. The reaction mixture was concentrated under reduced pressure and the oily residue thus obtained was treated by silica gel chromatography. The solvent was distilled and thus 8.48 g of phososphoric acid diester was obtained.

$^1$H-NMR(CD$_3$OD, δ ppm):
0.86 (d, 12H, methyl proton)
1.75 (t, 2H, methyl proton)
2.04, 2.10, 2.13 (s, 9H, methyl proton)
2.55 (t, 2H, methylene proton)
3.50–4.30 (m, 5H, glycerol site, methylene proton and methyl proton)

$^{31}$P-NMR(internal phosphoric acid standard, CD$_3$OD, δ ppm):
4.23 (α-compound)

EXAMPLE 5

5.0 g of the phosphoric acid diester obtained in Example 4 was dissolved in 15 ml of methyl alcohol. Then, a methyl alcohol solution of sodium hydroxide was gradually added thereto until the resulting mixture became neutral.

After completion of the addition, the resulting mixture was added dropwise to acetone, and white precipitate thus formed was washed with acetone and dried, whereby 3.91 g of white powdery crystals were obtained. $^1$H-NMR (CD$_3$OD, δ ppm):
0.85 (d, 12H methyl proton),
1.73 (t, 2H methylene proton),
2.05, 2.10, 2.14 (s, 9H methyl proton),
2.55 (t, 2H methylene proton),
3.50–4.30 (m, 5H glycerol site, methylene proton and methyl proton).
−P-NMR (internal phosphoric acid standard, CD$_3$OD, δppm):
3.21 (α-compound)
FT-IR (KBr, cm$^{-1}$)

| FT-IR (KBr, cm$^{-1}$) | |
|---|---|
| 3300–2800 | Br. s P(O)OH |
| 2932 | C—H stretching vibration |
| 1230 | P=O stretching vibration (phosphate) |
| 945 | P—O—C stretching vibration (aromatic). |

EXAMPLE 6

5.0 g of the phosphoric acid diester obtained in Example 4 was dissolved in 15 ml of methyl alcohol. Then, a methyl alcohol solution of potassium hydroxide was gradually added thereto until the resulting mixture became neutral.

After completion of the addition, the resulting mixture was added dropwise to acetone, and white precipitate thus formed was washed with acetone and dried, whereby 3.72 g of white powdery crystals were obtained.

$^1$H-NMR (CD$_3$OD, δ ppm): 0.86 (d, 12H methyl proton), 1.73 (t, 2H methylene proton), 2.05, 2.10, 2.14 (s, 9H methyl proton), 2.56 (t, 2H methylene proton), 3.50–4.30 (m, 5H glycerol site, methylene proton and methyl proton).
−P-NMR (internal phosphoric acid standard, CD$_3$OD, δ ppm):
3.20 (α-compound)

| FT-IR (KBr, cm$^{-1}$) | |
|---|---|
| 3300–2800 | Br. s P(O)OH |
| 2930 | C—H stretching vibration |
| 1230 | P=O stretching vibration (phosphate) |
| 945 | P—O—C stretching vibration (aromatic). |

FORMULATION EXAMPLE 1: Preparation of cosmetic lotion

The following components were blended at the ratio as specified below. Thus a cosmetic lotion was prepared in a conventional manner.

| | wt. % |
|---|---|
| Tocopherol glycerol diphosphate sodium salt | 2.0 |
| Ethanol | 10.0 |
| Polyoxyethylene lauryl ether | 1.0 |
| Propylene glycol | 3.0 |
| Perfume | q.s. |
| Colorant | q.s. |
| Preservative | q.s. |
| Purified water | the balance |

FORMULATION EXAMPLE 2: Preparation of milky lotion

The following components were blended at the ratio as specified below. Thus a milky lotion was prepared in a conventional manner.

| | wt. % |
|---|---|
| Tocopherol glycerol diphosphate potassium salt | 3.0 |
| Stearic acid | 1.0 |
| Cetanol | 2.5 |
| Vaseline | 3.0 |
| Polyoxyethylene sorbitan monolaurylate | 1.5 |
| Glycerol | 5.0 |
| Perfume | q.s. |
| Preservative | q.s. |

| | wt. % |
|---|---|
| Purified water | the balance |

TEST EXAMPLE 1: Solubility test

Water solubilities (at 20° C.) of tocopherol, tocopherol acetate, tocopherol phosphate disodium salt and tocopherol glycerol diphosphate sodium salt were examined. While tocopherol and tocopherol acetate were insoluble in water, tocopherol phosphate disodium salt showed a water-solubility of 0.27% and tocopherol glycerol diphosphate sodium salt showed a water-solubility of 3.0%.

TEST EXAMPLE 2: Stability test

Stabilities of tocopherol glycerol diphosphate sodium salt (purity: 96.2%) and tocopherol acetate (purity: 99% or above) were examined at a high humidity (90% RH or above) at a temperature of 50° C. After 3 months, tocopherol glycerol diphosphate sodium salt showed a purity of 95.2%, whereas tocopherol acetate showed a purity of 95%.

TEST EXAMPLE 3: Hair-nourishing test

Hairs at the head areas (1×1 cm) of male ddy mice (aged 8 weeks, each group having 5 animals) were pulled out with a pair of tweezers. From the day 3 following the removal of the hairs, 30 μl/day of a 50% ethanol aqueous solution containing 1% of each test compound as listed below was applied for 18 days continuously. After 18 days, several ten hairs growing newly were pulled out and 10 hairs were selected at random. Then the length of each hair was measured and the average was calculated to thereby give the test data as shown in Table 1.

TABLE 1

| Test compound | Hair length (mm) | Change (%) |
|---|---|---|
| Control | 4.215 ± 0.23 | — |
| VEPG-NA*[1] | 4.756 ± 0.17 | 12.83 |
| VEPG-K*[2] | 4.732 ± 0.16 | 12.27 |
| Minoxidil | 4.029 ± 0.21 | −5.42 |

*[1]Tocopherol glycerol diphosphate sodium salt
*[2]Tocopherol glycerol diphosphate potassium salt It is seen from the results that the test solutions containing tocopherol glycerol diphosphate alkali metal salts showed remarkable hair-nourishing effects. None of these test solutions caused any skin irritation.

While the invention has been described in detail and with reference to specific embodiments thereof, it will be apparent to one skilled in the art that various changes and modifications can be made therein without departing from the spirits and scope thereof.

What is claimed is:

1. A benzopyran derivative represented by formula (I):

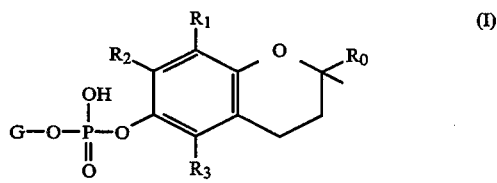

wherein $R_0$ represents an alkyl or alkenyl group having 10 to 20 carbon atoms; $R_1$ to $R_3$ each represent a methyl group or a hydrogen atom; and G represents a —$CH_2CH(OH)CH_2OH$ or —$CH(CH_2OH)_2$ group; or a salt thereof.

2. The benzopyran derivative or a salt thereof as in claim 1, wherein $R_0$ is —$C_{16}H_{33}$.

3. The benzopyran derivative or a salt thereof as in claim 1, wherein G represents a —$CH_2CH(OH)CH_2OH$ group.

4. The benzopyran derivative or a salt thereof as in claim 1, which is a pharmacologically acceptable salt.

5. The benzopyran derivative or a salt thereof as in claim 4, which is an alkali metal salt.

6. A cosmetic containing a benzopyran derivative represented by formula (I):

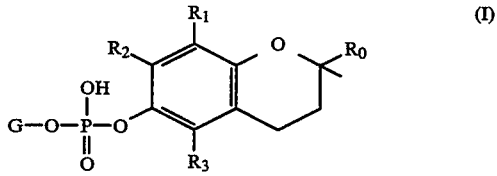

wherein $R_0$ represents an alkyl or alkenyl group having 10 to 20 carbon atoms; $R_1$ to $R_3$ each represent a methyl group or a hydrogen atom; and G represents a —$CH_2CH(OH)CH_2OH$ or —$CH(CH_2OH)_2$ group; or a salt thereof.

7. The cosmetic as in claim 6, wherein $R_0$ in formula (I) is —$C_{16}H_{33}$.

* * * * *